United States Patent [19]

Williams

[11] 4,139,775
[45] Feb. 13, 1979

[54] RADIOGRAPHY
[75] Inventor: Anthony M. Williams, Iver, England
[73] Assignee: EMI Limited, Hayes, England
[21] Appl. No.: 816,686
[22] Filed: Jul. 18, 1977
[30] Foreign Application Priority Data
  Jul. 28, 1976 [GB] United Kingdom .............. 31365/76
[51] Int. Cl.² ..................... G01T 1/20; G01M 23/00
[52] U.S. Cl. .................................. 250/445 T; 250/491
[58] Field of Search ............. 250/445 R, 445 T, 454,
  250/490, 491, 363, 366

[56] References Cited
U.S. PATENT DOCUMENTS

| | | | |
|---|---|---|---|
| 3,922,552 | 11/1975 | Ledley | 250/445 T |
| 3,986,031 | 10/1976 | Chekroun | 250/445 T |
| 4,031,395 | 6/1977 | LeMay | 250/445 T |

Primary Examiner—Bruce C. Anderson
Attorney, Agent, or Firm—Cooper, Dunham, Clark, Griffin & Moran

[57] ABSTRACT

A mechanical arrangement for use in computerized tomographic apparatus so as to permit the examination of volumetric body slices and body slices tilted with respect to the examination axis is described. The radiation source is mounted on an inner tilt frame which can rotate, by way of a lockable bearing, in an outer tilt frame which can be tilted relative to a sub frame which can be locked or free relative to the main frame of the apparatus. The outer tilt frame can also rotate, relative to the main frame, in a lockable bearing.

5 Claims, 1 Drawing Figure

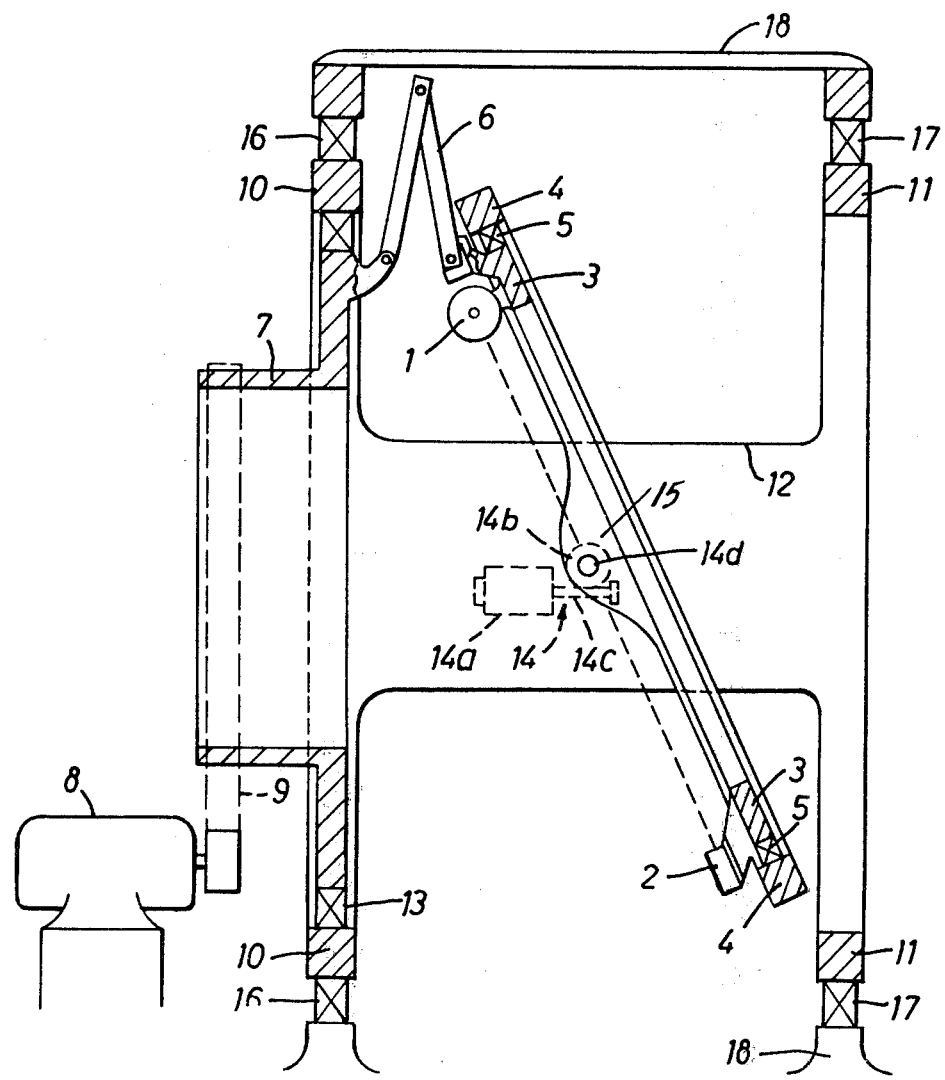

RADIOGRAPHY

The present invention relates to radiography, and it relates especially to that branch of radiography which has become known as computerised axial tomography, or briefly C.A.T.

Apparatus for performing C.A.T. is described and claimed in U.S. Pat. No. 3,778,614 and consists in essence of a scanning system, which produces output signals indicative of the absorption suffered by penetrating radiation, such as X-radiation, on traversing each of a large number of paths through a selected region of the body, and a processing system which receives the output signals and processes them to produce a representation of the variation of absorption of the radiation over the aforementioned region.

Different scanning techniques are described and claimed in U.S. Pat. No. 3,946,234 and in U.S. Pat. No. 4,035,647 for example. A different processing technique is described and claimed in U.S. Pat. No. 3,924,129.

The present invention relates to a scanning technique of the kind generally disclosed in United States Patent Application Ser. No. 790,474, by means of which it is possible to produce output signals relating to regions of the body which comprise transverse or slanted slices or alternatively to volumetric regions which conform to the shape of a concave lens, and has the object of providing an alternative scanning structure to achieve the same end.

According to the invention there is provided a scanning structure for scanning a source of radiation around a patient during a radiographic examination of the patient, the structure comprising: a static main frame having an annular portion surrounding an aperture in which the patient's body is disposed; a frame member having an annular flange coaxial with, and of smaller radius than, said annular portion, a first lockable bearing disposed between said flange and said annular portion of said main frame, an annular ring member coaxial with, and of smaller diameter than, said annular flange, a second lockable bearing disposed between said ring member and said flange, the axes of said ring member, said flange and said annular portion of said main frame extending longitudinally of said patient's body, an outer tilt frame of annular form pivotally mounted to said frame member, an inner tilt frame, also of annular form, disposed within said outer tilt frame and supporting said source, a third lockable bearing disposed between said inner and outer tilt frames and a drive link extensible in the direction of said axes but substantially rigid in a direction tangential of the scanning movement coupling said inner tilt frame to said ring member; the inner tilt frame encircling the patient's body, means for causing said ring member to rotate, about its axis, around the patient's body, causing said inner tilt frame to rotate therewith by means of said drive link at an attitude dependent upon the pivotal position, relative to said frame member, adapted by said outer tilt frame, and means for selectively locking one or more of said lockable bearings, in dependence upon the motion, relative to the patient, required of said source.

In order that the invention may be clearly understood and readily carried into effect, one embodiment thereof will now be described, by way of example only, with reference to the accompanying drawings the single FIGURE of which shows in cross-sectional side elevation, a scanning structure in accordance with one example of the invention.

Referring now to the drawing, a source of penetrating radiation, constituted by an X-ray tube 1, and a bank of collimated detectors 2 are fixed to an inner tilt frame 3 which is located within an outer tilt frame 4 and can rotate relative thereto by virtue of a bearing 5 provided between the two tilt frames. The bearing 5 can also be locked so as to constrain the two tilt frames to rotate together.

The inner tilt frame 3 is connected via a torsion drive link 6 to a driven ring member 7; the member 7 being driven by means of a motor 8 through a belt drive 9. Ring member 7 is surrounded by one of two flanges 10 and 11 attached to either end of a frame member 12 which comprises two elongated support members, only one of which can be seen in the drawing. An inner bearing 13 is provided between the ring member 7 and the inner surface of flange 10. Attached to a part of the apparatus which rotates with the outer tilt frame 4 is an actuator 14 which comprises an electric motor 14a driving a gear wheel 14b by way of a worm gear 14c. The gear wheel 14b is attached to a rod 14d which is connected to the outer tilt frame 4 and passes through the member 12 to form part of a pivot 15. There is a similar pivot on the other side of member 12. Actuation of the actuator 14 can cause the outer tilt frame 4 to tilt about the two pivots, such as 15, relative to the frame member 12. Different arrangements for the actuator 14 are, of course possible. For example a motor driven lead screw or other extensible member can be used. The two flanges 10 and 11 are mounted, via respective bearings 16 and 17, to a static main frame 18.

The bearings 13, 16 and 17 can, like the bearing 5, be locked if desired to prevent relative rotation of the components on either side thereof.

In operation; if the structure is to scan an upright or slanted slice through a body (not shown but assumed to be lying supine or prone within the member 12) the bearings 16 and 17 are locked, so that the outer tilt frame 4 remains static and the tube 1 and detectors 2 rotate within frame 4, by virtue of bearing 5, being driven from the ring member 7 via the torsion drive link 6. The angle of the slice is set by the operation of the actuator 14 and the attitude of the slice relative to the body is set by initially rotating the whole structure on bearings 16 and 17 prior to locking those bearings.

If the aforementioned volumeteric scan is to be effected, the bearings 13 and 5 are locked. As the structure rotates, in bearings 16 and 17, about the body, the actuator 14 is moved slowly to vary the angle of tilt of the frames 3 and 4 continuously during the course of several revolutions of the tilt frames 3 and 4 around the body.

More details of the two scanning techniques (i.e., slice scanning and volumetric scanning) and of techniques for processing the output signals provided by a scanning structure of the kind described herein can be found in the aforementioned U.S. Pat. App. Ser. No. 790,474 the disclosure of which is incorporated herein by reference.

What I claim is:

1. A scanning structure for scanning a source of radiation around a patient during a radiographic examination of the patient, the structure comprising:
   a static main frame having an annular portion surrounding an aperture in which the patient's body is disposed; a frame member having an annular flange coaxial with, and of smaller radius than, said annular portion, a first lockable bearing disposed between said flange and said annular portion of said main frame, an annular ring member coaxial with, and of smaller diameter than, said annular flange, a second lockable bearing disposed between said ring member and said flange, the axes of said ring member, said flange and said annular portion of said main frame extending longitudinally of said patient's body, an outer tilt frame of annular form pivotally mounted to said ring member, an inner tilt frame, also of annular form, disposed within said outer tilt frame and supporting said source, a third lockable bearing disposed between said inner and outer tilt frames and a drive link extensible in the direction of said axes but substantially rigid in a direction tangential of the scanning movement coupling said inner tilt frame to said ring member; the inner tilt frame encircling the patient's body, means for causing said ring member to rotate, about its axis, around the patient's body, causing said inner tilt frame to rotate therewith by means of said drive link at an attitude dependent upon the pivotal position, relative to said frame member, adopted by said outer tilt frame, and means for selectively locking one or more of said lockable bearings, in dependence upon the motion, relative to the patient, required of said source.

2. A scanning structure according to claim 1 wherein, to permit said source to execute a scanning motion in a single upright or tilted plane relative to the patient's body, said selective locking means include means for locking said first bearing but not said second and third bearings, the attitude of said plane being determined by the pivotal condition of said outer tilt frame relative to said frame member and accommodated by extension of said drive link.

3. A structure according to claim 2 including pivot control means for determining and controlling the pivotal condition of said outer tilt frame relative to said frame member.

4. A structure according to claim 3 wherein said pivot control means includes a gear wheel and a rod attached to said outer tilt frame and a motor driven worm gear attached to said frame member; said worm gear being disposed to drive said gear wheel.

5. A structure according to claim 1 wherein, to permit said source to execute a plurality of consecutive scans around the patient while simultaneously traversing longitudinally along the patient, said selective locking means include means for locking said second and third bearings but not said first bearing, the attitude of the outer tilt frame relative to said frame member being variably controlled during the scanning.

* * * * *